US00PP30095P3

(12) United States Plant Patent
Brand

(10) Patent No.: US PP30,095 P3
(45) Date of Patent: Jan. 15, 2019

(54) BARBERRY PLANT NAMED 'UCONNBTCP4N'

(50) Latin Name: *Berberis thunbergii*
Varietal Denomination: UCONNBTCP4N

(71) Applicant: University of Connecticut, Farmington, CT (US)

(72) Inventor: Mark Brand, Farmington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 15/330,048

(22) Filed: Jul. 30, 2016

(65) Prior Publication Data

US 2018/0035586 P1 Feb. 1, 2018

(51) Int. Cl.
*A01H 5/00* (2018.01)
*A01H 5/08* (2018.01)

(52) U.S. Cl.
USPC ..... Plt./241
CPC ..... *A01H 5/08* (2013.01)

(58) Field of Classification Search
USPC ..... Plt./241
See application file for complete search history.

(56) References Cited

U.S. PATENT DOCUMENTS

PP8,215 P 4/1993 Moretti

OTHER PUBLICATIONS

Lehrer et al (Scientia Horticulturae. 2008. 119:67-71).*
Co-pending U.S. Appl. No. 15/330,051, filed Jul. 30, 2016.
Co-pending U.S. Appl. No. 15/330,050, filed Jul. 30, 2016.
Co-pending U.S. Appl. No. 15/330,049, filed Jul. 30, 2016.

* cited by examiner

*Primary Examiner* — Keith O. Robinson
(74) *Attorney, Agent, or Firm* — Michael Best & Friedrich LLP

(57) ABSTRACT

The present invention relates to a new and distinct cultivar of Barberry plant, botanically known as *Berberis thunbergii* and hereinafter referred to by the name 'UCONNBTCP4N'. The unique characteristics of this new Barberry plant include essentially seed sterile; compact, dense, low-growing habit; thick and slightly leathery purple-red spring and summer foliage; adaptable to many landscape situations; resistant to black stem rust disease; and winter cold hardy to at least −26° C.

6 Drawing Sheets

FEDERAL FUNDING

This invention was made with government support under 2015-31200-06009 awarded by the USDA. The government has certain rights in the invention.

BACKGROUND OF THE INVENTION

The present invention relates to a new and distinct cultivar of Barberry plant, botanically known as *Berberis thunbergii* and hereinafter referred to by the name 'UCONNBTCP4N'.

The new Barberry plant is a product of a planned breeding program conducted in Storrs, Conn. The new barberry plant originated from *Berberis thunbergii* 'Crimson Pygmy' (synonym *Berberis thunbergii* 'Atropurpurea Nana') through the use of the mitotic inhibitor colchicine to create an autotetraploid form of the plant. Nopaternal plant is involved in the creation of 'UCONNBTCP4N'. *Berberis thunbergii* 'Crimson Pygmy' is not patented and has been used in the nursery industry since 1942. Briefly, nodal explants of in vitro *Berberis thunbergii* 'Crimson Pygmy' shoot cultures were exposed to 0.1% colchicine for 24 hours in liquid culture media. Nodes were then grown out in tissue culture and shoots were segregated into individual shoots and cultured further. Ploidy of individual shoot cultures was then determined by flow cytometry. Shoots converted to tetraploidy were then multiplied in vitro, rooted in vitro, and acclimated to the greenhouse. Eventually, tetraploid plants were grown outdoors in containers and then in the field. Tetraploidy was confirmed multiple times by flow cytometry when plants were in containers and in the field.

Tetraploid plants were created in late 2004 and early 2005. Tetraploid plants were acclimated to the greenhouse, and then to outdoor container culture in spring and summer of 2005. Tetraploid plants were grown outdoors in containers during 2005, 2006 and 2007. In spring 2008, tetraploid plants were planted in the field for long term evaluation. Diploid *Berberis thunbergii* 'Crimson Pygmy' plants from tissue culture were grown alongside tetraploid plants to serve as control plants. During the growing seasons of 2012, 2013, and 2014, tetraploid plants established in the field were evaluated for fruit production, seed production, seed germination and seedling ploidy in comparison to diploid control plants.

Asexual reproduction of *Berberis thunbergii* 'UCONNBTCP4N' by either micropropagation via tissue culture (since 2006) or by softwood stem cuttings (since 2012) made in late June through early July in a controlled laboratory, greenhouse or container nursery environment has shown that the unique features of this new barberry plant are stable and reproduced true-to-type in successive generations of asexual reproduction.

SUMMARY OF THE INVENTION

Plants of the new Barberry have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of the new Barberry plant: dense habit growing to 45-60 cm tall by 90-105 cm wide in 10 years; purple-red spring and summer foliage; foliage thick and slightly leathery, held on stout stems; fall foliage color is purple-red-orange; small yellow and red flowers held in clusters of 3 to 6 flowers, in late April-early May, sometimes cymous; fruit is red, ripening in October, ellipsoidal, 7-10 mm long and 4-5 mm wide; cold hardy in winter to at least −26° C.; seed production is 0.2% that of standard, diploid *Berberis thunbergii* 'Crimson Pygmy', so it is essentially seed sterile; tested to be resistant to black stem rust by the USDA Cereal Diseases Laboratory in St. Paul, Minn.

These characteristics in combination distinguish *Berberis thunbergii* 'UCONNBTCP4N' as a new and distinct Barberry plant:

1. essentially seed sterile;
2. compact, dense, low-growing habit;
3. thick and slightly leathery purple-red spring and summer foliage;
4. adaptable to many landscape situations;
5. resistant to black stem rust disease; and
6. winter cold hardy to at least −26° C.;

Plants of the new Barberry can be compared to plants of the female parent *Berberis thunbergii* 'Crimson Pygmy'. Plants of the new Barberry differ primarily from plants of *Berberis thunbergii* 'Crimson Pygmy' in that *Berberis thunbergii* 'UCONNBTCP4N' is essentially sterile, while same age 'Crimson Pygmy' plants produce over 8,000 seeds per plant per year. In addition, *Berberis thunbergii* 'UCONNBTCP4N' grows approximately 10% larger than 'Crimson Pygmy' and has stouter stems and thicker, more leathery foliage.

Plants of the new Barberry can be compared to the unpatented commercial variety *Berberis* 'Emerald Carousel'. These varieties are similar in most horticultural characteristics; however 'UCONNBTCP4N' differs in the following:

1. Very compact plant habit, whereas this comparator is a large plant with a spreading habit.
2. Purple-red leaf color, whereas this comparator has a green leaf color.
3. Very low or no female fertility or fruit production, whereas this comparator is highly fruitful.

BRIEF DESCRIPTION OF THE PHOTOGRAPHS

The accompanying colored photographs illustrate the overall appearance of the new Barberry plant showing the colors as true as it is reasonably possible to obtain in colored reproductions of this type. Colors in the photographs may differ slightly from the color values cited in the detailed botanical description which accurately describe the colors of the new Barberry plant.

Figure 1:
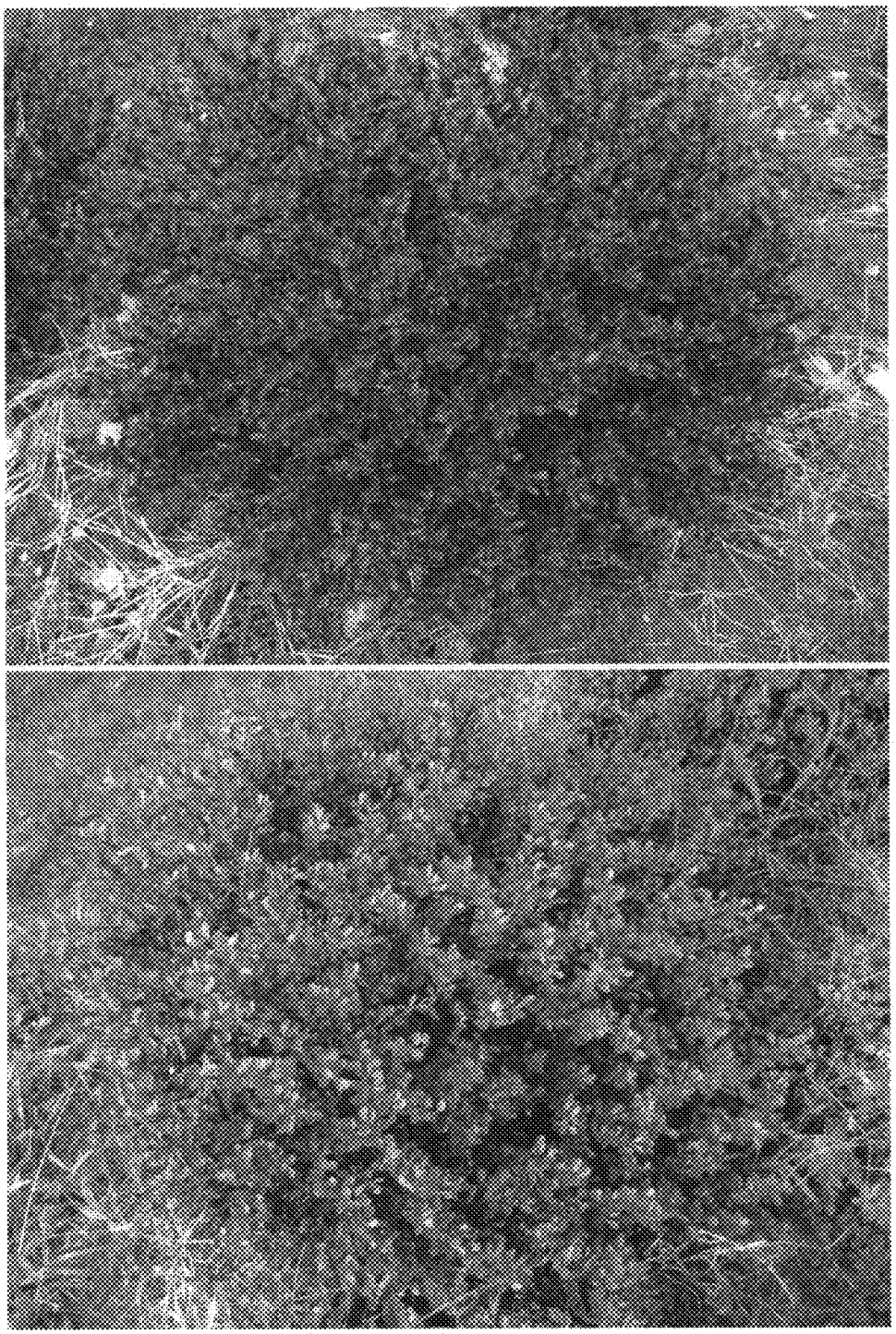
FIG. 1 is a photograph showing a field grown plant of 'UCONNBTCP4N' as it appears in spring (top image) and then later in the summer (bottom image).
Figure 2:
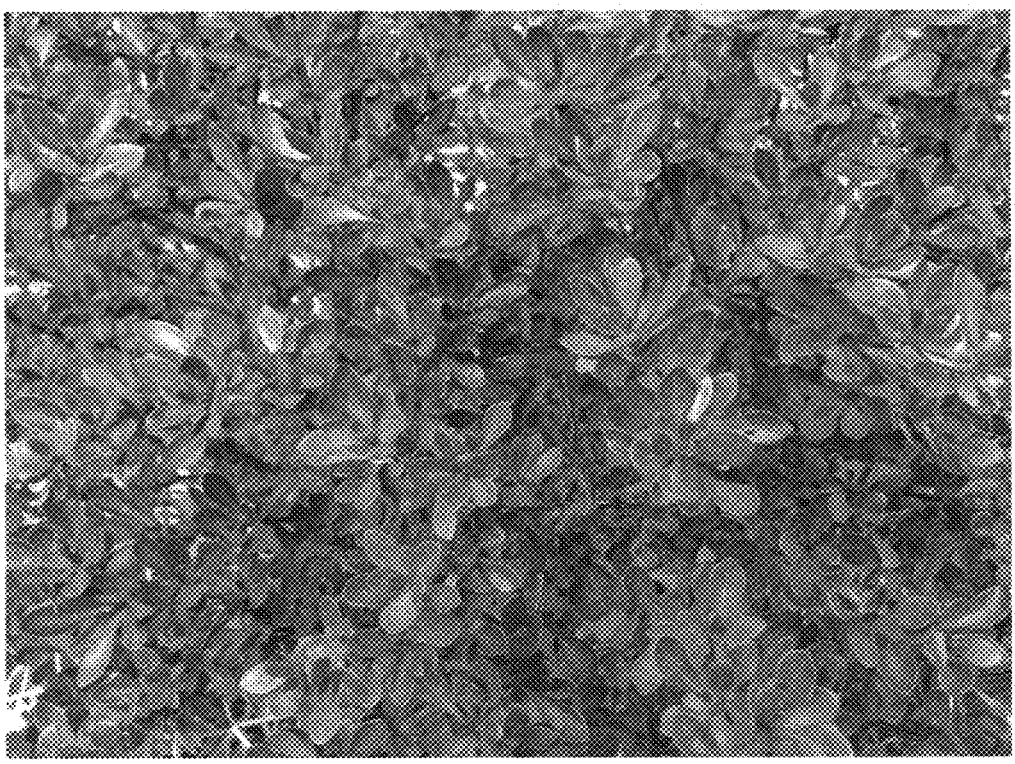
FIG. 2 is a photograph showing a close up of 'UCONNBTCP4N' foliage in the spring prior to long shoot extension.
Figure 3:
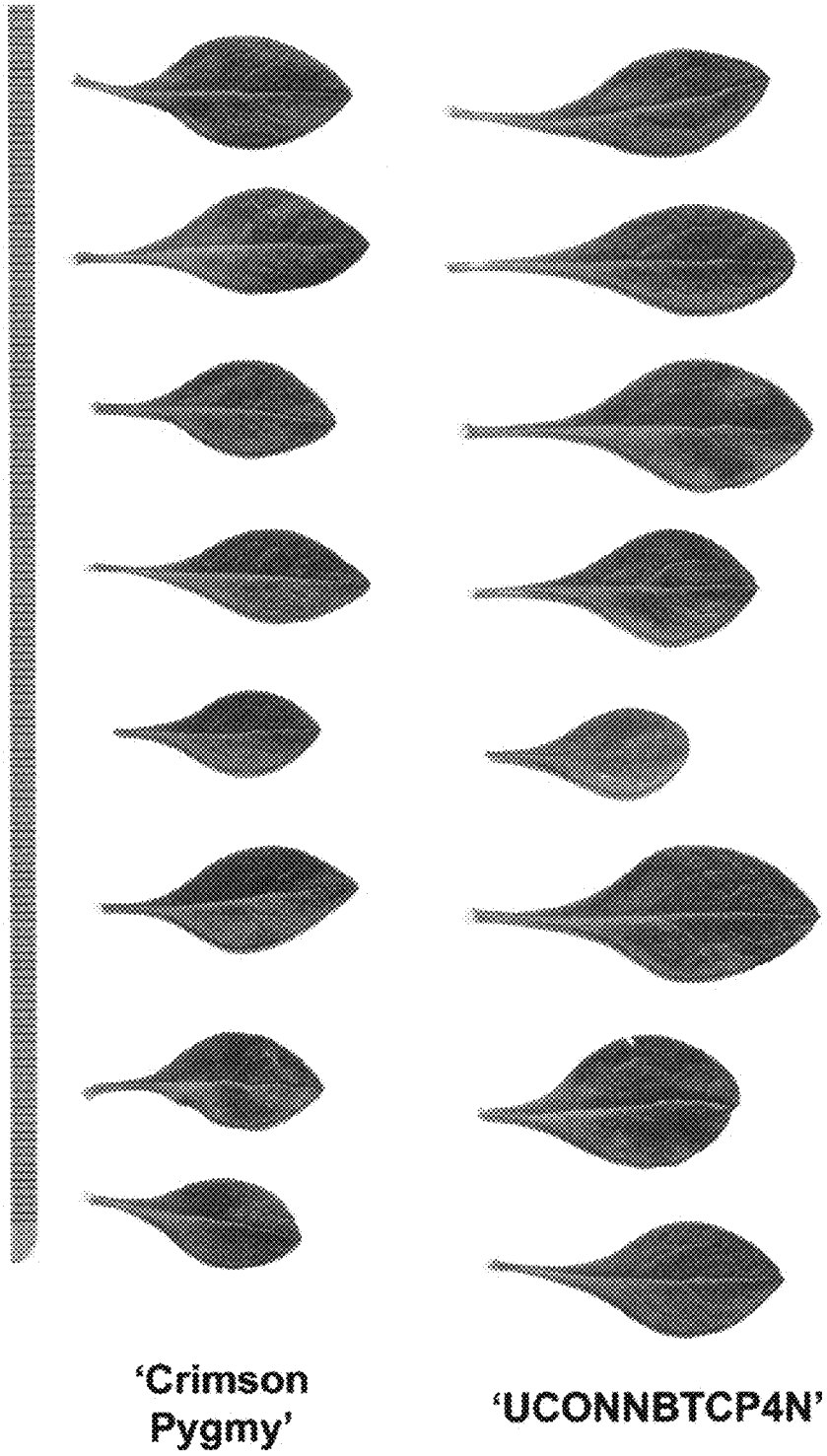
FIG. 3 is a photograph showing a close up comparison of leaves from 'Crimson Pygmy' (left column) and 'UCONNBTCP4N' (right column).
Figure 4:
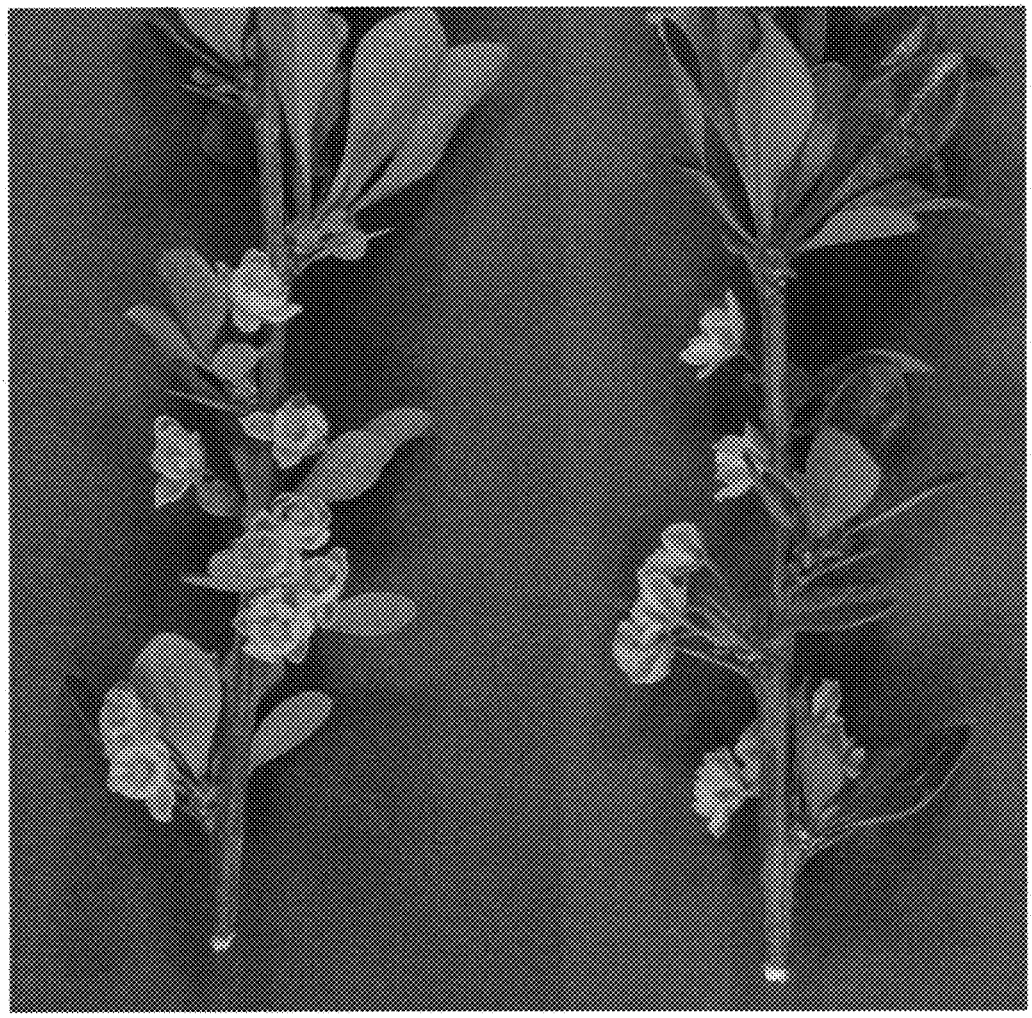

FIG. 4 contains photographs showing the flowers of 'UCONNBTCP4N'.

Figure 5:
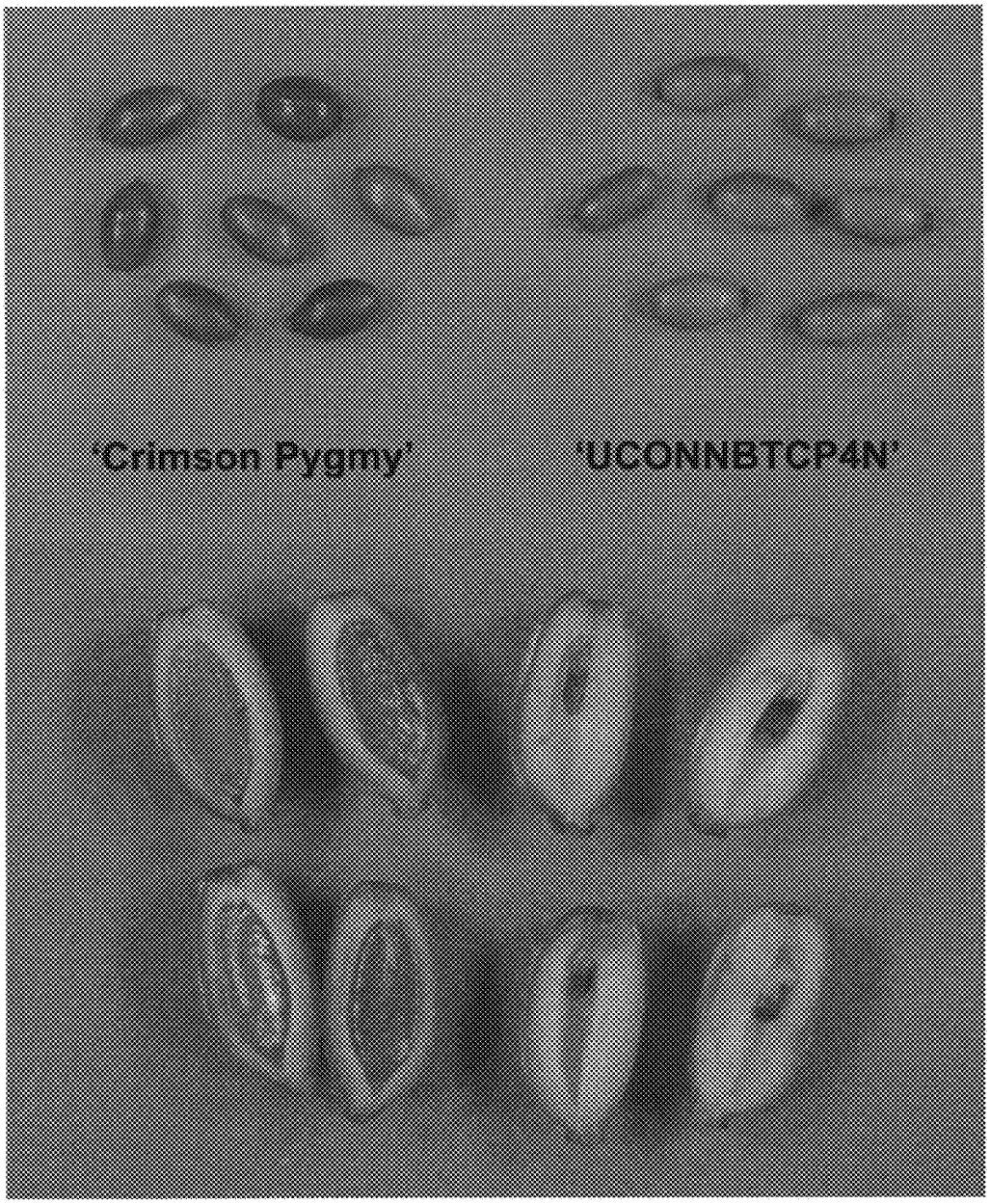

FIG. 5 contains photographs showing the intact fruits of 'Crimson Pygmy' (left) and 'UCONNBTCP4N' (right) in the top panel. The bottom panel shows fruits cut open to reveal ovary contents. Well-developed seeds are present in 'Crimson Pygmy' fruits (left), but seeds have aborted at an early stage within the fruits of 'UCONNBTCP4N' (right).

Figure 6:
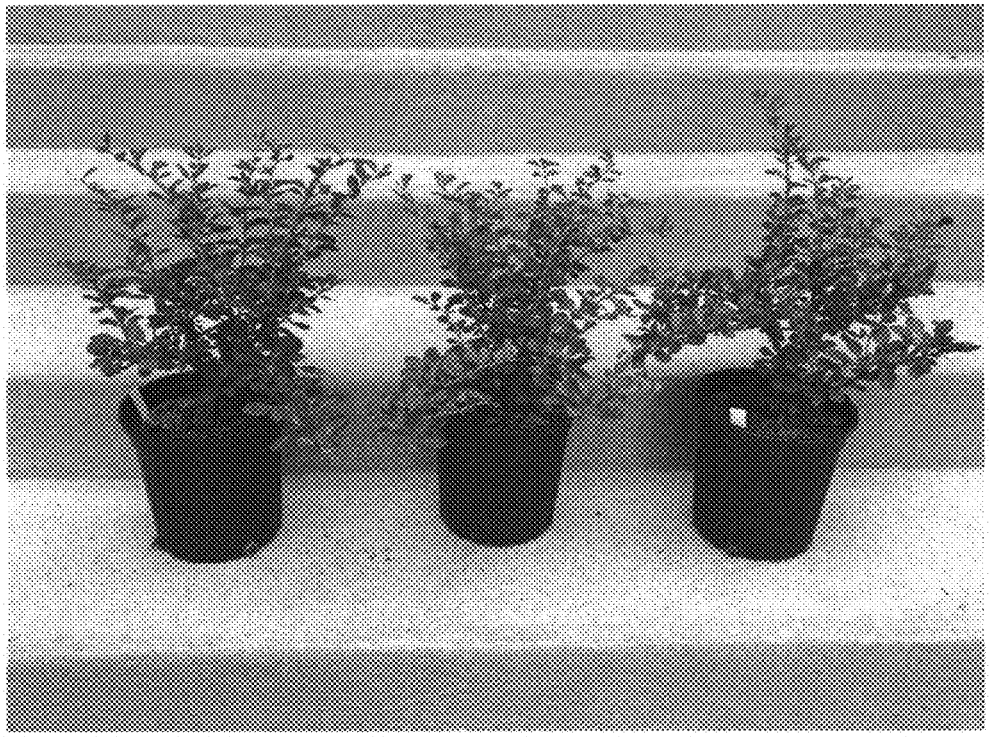

FIG. 6 is a photograph showing three container grown plants of 'UCONNBTCP4N' at the beginning of their second summer of growth since propagation. These plants were rooted from softwood cuttings two summers prior.

DETAILED BOTANICAL DESCRIPTION

The aforementioned photographs and following observations, measurements and values describe plants grown during the spring, summer, or fall in ground beds or container, in an outdoor nursery in Storrs, Conn. and under cultural practices which closely approximate commercial Barberry production. Plants used for most photographs and description were 10 years old. In the following detailed description, color references are made to The Royal Horticultural Society Colour Chart, 1995 Edition, except where general terms of ordinary dictionary significance are used.

Botanical classification: *Berberis thunbergii* 'UCONNBTCP4N'.

Parentage:

*Female, or seed, parent.*—Barberry *thunbergii* 'Crimson Pygmy', not patented.

*Male, or pollen, parent.*—Not applicable. Mitotic inhibitor colchicine was used to create an autotetraploid from a maternal parent only.

Propagation:

*Type.*—Softwood stem cutting.

*Time to initiate roots, summer.*—About 6 weeks at daytime temperatures between 75-90° F.

*Time to produce a rooted young plant, summer.*—About 8-12 weeks at temperatures between 75-90° F.

*Root description.*—2-6 roots per cutting, yellow to brown in color and not effectively measured with a color chart.

*Rooting habit.*—Fibrous root system develops from the initial adventitious roots.

Plant description:

*Plant form and growth habit.*—Low, dense, mounded, compact plant, typically wider than tall.

*Plant height.*—About 45-60 cm tall in 10 years.

*Plant diameter (area of spread).*—About 90-105 cm wide in 10 years.

*Plant vigor.*—Medium.

Lateral branch description:

*Length.*—About 15 cm, typically between 10-20 cm.

*Diameter.*—About 2 mm to 3 mm.

*Internode length.*—About 15 mm, typically between 10-20 mm.

*Aspect.*—Upright and arching outward from the plant center.

*Strength.*—Firm and stiff.

*Texture.*—Fine.

*Color.*—Close to 146D yellow-green (new, current. season shoots).

*Thorns.*—Quantity: single at most nodes. Length: 10-12 mm. Width at the base: 1 mm. Color: 146D at base, changing to 183 B at tip.

Leaf description:

*Arrangement.*—Whorled in rosette on spur shoots; alternate down long shoots, but typically 2-3 leaves at each node.

*Length.*—About 35 mm, typically ranging from 20-50 mm.

*Width.*—About 18 mm, typically ranging from 14-21 mm.

*Shape.*—Obovate to spatulate-oblong.

*Apex.*—Typically obtuse, sometimes with small spine at tip.

*Base.*—Narrowing to only petiole; very acute.

*Margin.*—Entire.

*Texture, upper and lower surfaces.*—Glabrous.

*Venation pattern.*—pinnate.

*Color.*—Developing leaves, upper surface: Close to 183A and 183B greyed-purple group under high light conditions.

*Developing leaves, lower surface.*—186A greyed purple group at margins, changing to 191B greyed green in center under high light conditions.

*Fully expanded leaves, upper surface.*—Close to 187A greyed-purple group and 200A brown group under high light conditions. Shaded leaves 137A green group.

*Fully expanded leaves, lower surface.*—Close to 191A greyed-green group under high light conditions. Shaded leaves 137C green group.

*Petiole.*—Length: About 1-14 mm. Diameter: About 1 mm. Texture, upper and lower surfaces: glabrous. Color, upper and lower surfaces: RHS 187A greyed-purple and 200A brown in high light.

*Persistence of foliage.*—Deciduous.

*Glossiness of the leaf.*—Medium.

Flower description:

*Flower arrangement and habit.*—Typically cymous.

*Fragrance.*—None noted.

*Natural flowering season.*—April in Storrs, Conn.

*Flower longevity.*—7 to 14 days depending on weather conditions.

*Inflorescence length.*—About 15 mm; ranging from about 10-20 mm.

*Inflorescence diameter.*—About 22.5 mm; ranging from about 21-25 mm.

*Inflorescence type.*—Umbellate fascicles. Axial occurring along underside of branches.

*Number of flowers per inflorescence.*—3-6.

*Flower diameter.*—About 12 mm; ranging from 10-13 mm.

*Flower length (height).*—About 5.75 mm; ranging from 5-7 mm.

*Flower buds.*—Length: About 4 mm. Diameter: About 6 mm. Shape: Rounded. Color: Close to 53A and 53B, red group.

*Petals.*—Arrangement: 6 petals in a single whorl.

*Length.*—About 4-5 mm.

*Width.*—About 3-4 mm.

*Shape.*—Cupped.

*Apex.*—Rounded to acute.

*Margin.*—Smooth.

*Texture, upper and lower surfaces.*—Both glabrous.

*Color.*—When opening and fully open, adaxial and abaxial surfaces: 12C yellow group.

*Sepals.*—Arrangement: 6 to 8 sepals in a single whorl. Length: About 7 mm. Width: About 4 mm. Shape: cupped. Apex: rounded to acute. Base: straight-sided, tapering. Margin: smooth. Texture, upper and lower surfaces: glabrous. Color: Fully developed, adaxial surface: Close to 12C, yellow group, with colors from abaxial side showing through. Fully developed, abaxial surface: Close to 53A and 53B, red group.

*Peduncles.*—Length: About 4-14 mm. Diameter: About 1 mm. Aspect: About 60 degrees from lateral branch axis. Color: Close to 53A and 53B, red group.

*Pedicels.*—Length: About 4-6 mm. Diameter: About 1 mm. Aspect: About 45-60 degree from peduncle axis. Color: Close to 53A and 53B, red group.

*Reproductive organs.*—Stamens: Quantity: 6. Anther shape: flat to cupped, narrow. Anther length: About 4 mm. Anther color: Close to 12C. Pollen amount: Scarce and sticky. Pollen color: Near RHS yellow 12A. Pistils: Quantity: 1 per flower. Pistil length: About 3 mm. Style length: About 1-2 mm. Style color: Close to 144C and 145B. Stigma color: Close to 144C and 145B. Ovary color: Close to 144C and 145B. Seeds and fruits: Seed and fruit development have been observed on plants of the new Barberry. Fruits are almost always devoid of seeds. 'UCONNBTCP4N' produces only 0.2% of the seed produced by 'Crimson Pygmy', even if fruits are produced. Fruit shape: Elliptical, 8-11 mm long and ~5 mm in diameter. Fruit color: RHS color near red 53B. Fruit waxiness: Glossy.

Garden performance: Plants of the new Barberry have been observed to have excellent garden performance and tolerate a wide range of environmental conditions and temperatures ranging from about −26*C to about 40° C.

Pathogen & pest resistance: Plants of the new Barberry have been observed to be resistant to blackstem rust (*Puccinia graminis* f. sp. *tritici*). Plants of the new Barberry have not been shown to be resistant to pests and other pathogens common to Barberry plants.

It is claimed:

1. A new and distinct Barberry plant named 'UCONNBTCP4N' as illustrated and described.

* * * * *